US012630794B2

(12) United States Patent
Hansen et al.

(10) Patent No.: US 12,630,794 B2
(45) Date of Patent: May 19, 2026

(54) BIOREACTORS FOR ORBITALLY SHAKING CELL CULTURES, IN PARTICULAR SUSPENSION CULTURES

(71) Applicant: EVONIK OPERATIONS GMBH, Essen (DE)

(72) Inventors: Sven Hansen, Frankfurt (DE); Wilfried Blümke, Schöneck (DE); Fabian Bülow, Heidelberg (DE); Andreas Gumprecht, Frankfurt am Main (DE)

(73) Assignee: Evonik Operations GmbH, Essen (DE)

( * ) Notice: Subject to any disclaimer, the term of this patent is extended or adjusted under 35 U.S.C. 154(b) by 745 days.

(21) Appl. No.: 17/924,320

(22) PCT Filed: May 4, 2021

(86) PCT No.: PCT/EP2021/061630
§ 371 (c)(1),
(2) Date: Nov. 9, 2022

(87) PCT Pub. No.: WO2021/228613
PCT Pub. Date: Nov. 18, 2021

(65) Prior Publication Data
US 2023/0183626 A1 Jun. 15, 2023

(30) Foreign Application Priority Data
May 13, 2020 (EP) .................................... 20174296

(51) Int. Cl.
*C12M 1/00* (2006.01)
*C12M 3/06* (2006.01)

(52) U.S. Cl.
CPC ............ *C12M 23/34* (2013.01); *C12M 27/16* (2013.01)

(58) Field of Classification Search
CPC ....... C12M 23/34; C12M 27/16; C12M 41/00
See application file for complete search history.

(56) References Cited

U.S. PATENT DOCUMENTS

| | | | | |
|---|---|---|---|---|
| 5,578,490 A | * | 11/1996 | Martinez Ubeira | ... C12M 23/12 435/305.3 |
| 9,328,374 B2 | | 5/2016 | Nordmann et al. | |

(Continued)

FOREIGN PATENT DOCUMENTS

| | | |
|---|---|---|
| DE | 10 2014 017 728 | 6/2016 |
| WO | WO 2010/056555 | 5/2010 |

(Continued)

OTHER PUBLICATIONS

International Search Report for corresponding PCT/EP2021/061630, May 4, 2021.

(Continued)

*Primary Examiner* — Liban M Hassan
(74) *Attorney, Agent, or Firm* — Law Office of: Michael A, Sanzo, LLC

(57) ABSTRACT

The present invention relates to. a bioreactor vessel (1) having an outer vessel wall (2) and a bottom (3), further comprising an integrated internal structure (4) providing at least two additional surfaces (4a), (4b) to the internal reactor space of said vessel, said internal structure (4) being spaced apart from said outer vessel wall (2), as well as to a process for growing biological cells using said bioreactor vessel.

20 Claims, 11 Drawing Sheets

(56)  References Cited

U.S. PATENT DOCUMENTS

| | | | | |
|---|---|---|---|---|
| 9,868,095 | B2 | 1/2018 | Selker et al. | |
| 2010/0248995 | A1 | 9/2010 | Kensy et al. | |
| 2011/0256624 | A1 | 10/2011 | Jenne et al. | |
| 2014/0178992 | A1 | 6/2014 | Nakashima et al. | |
| 2015/0252329 | A1* | 9/2015 | Ostrowski | C12M 23/04 |
| | | | | 435/395 |
| 2016/0160164 | A1 | 6/2016 | Salek et al. | |
| 2018/0112170 | A1* | 4/2018 | Kulinsky | C12M 29/04 |

FOREIGN PATENT DOCUMENTS

| | | |
|---|---|---|
| WO | WO 2014/120702 | 8/2014 |
| WO | WO 2015/013817 | 2/2015 |

OTHER PUBLICATIONS

Written Opinion of the International Searching Authority for corresponding PCT/EP2021/061630, May 4, 2021.

International Preliminary Report on Patentability for corresponding PCT/EP2021/061630, May 4, 2021.

European Search Report and Search Opinion for corresponding EP 20174296, filed May 13, 2020.

Hermann, et al., "Optical Method for the Determination of the Oxygen-Transfer Capacity of Small Bioreactors Based on Sulfite Oxidation," *Biotechnology & Bioengineering* 74(5):355-363 (2001).

Zhang, et al., "Shaken helical track bioreactors: Providing oxygen to high-density cultures of mammalian cells at volumes up to 1000 L by surface aeration with air," *N. Biotechnol.* 25(1):68-75 (Jun. 2008).

Zhu, et al., "Developing an orbitally shaken bioreactor featuring a hollow cylinder vessel wall," *J. Chem. Technol. Biotechnol.* 94(7):2212-2218 (May 2019).

* cited by examiner

A

B

A

B

A

B

BIOREACTORS FOR ORBITALLY SHAKING CELL CULTURES, IN PARTICULAR SUSPENSION CULTURES

CROSS REFERENCE TO RELATED APPLICATIONS

The present application is US national stage of international application PCT/EP2021/061630, which had an international filing date of May 4, 2021 and which was published on Nov. 18, 2021. The application claims priority to EP 20174296.2, filed on May 13, 2020. The content of these prior applications is hereby incorporated by reference in its entirety.

The present invention refers to bioreactor vessels for shaken cell cultures, in particular suspension cultures of any biological cell type, comprising an integrated internal structure providing at least two additional internal surfaces to the reactor space and a process for growing biological cells using said bioreactor vessel.

The growing of gas consuming, e.g. aerobic biological cells in suspension cell cultures requires—besides the provision of nutrients—the sufficient supply with e.g oxygen, thus, air input into the liquid culture. Orbitally shaken bioreactors are important types of bioreactors and are commonly available with culture volumes of from μl range up to 2000 1. Such reactors are easy to operate with low operating cost and therefore are a target for improving culturing performance. An ongoing demand of such bioreactor vessels is to increase the gas input into the cell culture liquid.

Increasing the air input into the culture liquid of shaken bioreactors has been considered e.g. in US 2010/0248995 A1, wherein bioreactors are described having a particularly formed cross section. In this document it is shown that reactors having a cross section with several rounded edges provide a clearly higher air input than commonly used bioreactors comprising baffles in their outer surface. The best mode has been shown to be a cross section appearing like a flower.

Zhang X W, Stettler M. et al. describe in N Biotechnol 35: 68-75 (2008) a bioreactor for mammalian cells of up to 1000 1 volume comprising a helical track attached to the inside surface of the container wall for increasing oxygen supply.

Zhu L., Song B. and Wang Z. describe in J. Chem Technol Biotechnol 94: 2212-2218 (2019) a bioreactor consisting of a hollow cylinder wall, wherein the cell culture is orbitally shaken in the hollow wall.

The object of the present invention was to provide a bioreactor vessel for biological cell cultures having a setup simply to prepare, yet effective in increasing the gas input into the cell culture.

This object is met by a bioreactor vessel as defined in the claims. The bioreactor provided by the present invention is effective in a process for growing biological cells under defined gas conditions.

According to the present description with "cell culture" is meant a culture of any biological cells, e.g. microorganisms like bacteria, archeae, algae, fungi (incl. yeast), virus/phage cultures (with suitable host cells), human or animal cells, like mammal, avian or insect cells, or plant cells. According to the invention the shaken cultures can be suspension cell cultures or adherent cell cultures, wherein suspension cultures are preferred. Particularly suspension cultures of microorganisms are in the focus of the present invention.

According to the invention the bioreactor vessel (1) has an outer vessel wall (2) and a bottom (3), and further comprises an integrated internal structure (4) providing at least two additional surfaces (4a), (4b) to the inner reactor space of said vessel, wherein said internal structure (4) being spaced apart from said outer vessel wall (2).

According to the invention the bioreactor vessel (1) can also comprise more than one internal structure (4), e.g. surrounding each other or being placed side-by-side, wherein said internal structures can have the same geometrical form or can differ from each other. If more than one internal structure (4) is integrated into the bioreactor vessel (1), there might be provided more than two additional surfaces (4a) and (4b), In the following the principle of the present invention is explained with reference to one integrated internal structure (4), however, it should be understood that more than one of such internal structures (4) can be placed into the bioreactor vessel (1), resulting in e.g. 4, 6, 8 or more additional surfaces.

It should be understood that the internal structure (4) is placed inside of the reactor chamber, i.e. inside the space surrounded by the outer vessel wall (2) of the vessel (1) (here also mentioned as the "inner reactor space" or simply "reactor space") in a way that a liquid comprised in the reactor chamber can come in contact with at least two surfaces (4a, 4b) of said internal structure (4).

Said internal structure (4) can comprise a wall providing an outer surface (4a) and an inner surface (4b), wherein said wall (i) has at least one opening (5) at least in the area closest to the bottom (3), or (ii) is spaced apart from the bottom (3), or (iii) has at least one opening and is spaced apart from the bottom (3). The term "outer surface" refers to the surface of the wall directed to the outer vessel wall (2), the "inner surface" is directed to the vessel center.

The wall of the internal structure (4) providing surfaces (4a) and (4b) can basically have the same or a similar geometrical shape as the outer vessel wall (2), so that the wall providing surfaces (4a) and (4b) extends inside the inner reactor space essentially parallel to the outer vessel wall (2). Thus, for example, if the outer vessel wall (2) is cylindrical, conical or elliptic, the wall of the internal structure (4) as well can be preferably cylindrical, conical or elliptic. Alternatively, the shape of the internal structure (4) and the outer vessel wall (2) can be different, e.g. they can be independently selected from cylindrical, conical elliptic or any other suitable shape. Further, if more than one internal structure (4) is present in the bioreactor vessel (1), the shape of the internal structures (4) present in the vessel (1) may be the same or may differ from each other. Any combination of suitable shapes of the outer vessel wall (2) and the internal structure(s) (4) shall be regarded as falling under the definition of the present invention. Preferred shapes are conical, cylindrical and elliptic, which can be combined in any combination. For example, the outer wall (2) of the vessel (1) can be conical and (at least one of) the internal structure(s) can be cylindrical or elliptic, the outer wall (2) of the vessel (1) can be cylindrical and (at least one of) the internal structure(s) can be conical or elliptic. In one preferred embodiment the outer wall (2) of the vessel (1) can be conical and (at least one of) the internal structure(s) can be cylindrical or vice versa, In another preferred embodiment both, the outer vessel wall (2) and at least one internal structure (4) having the wall providing said surfaces (4a) and (4b) are cylindric.

It is particularly preferred that the internal structure (4) providing surfaces (4a) and (4b) is placed inside the reactor space in a way so that in the non-operating state (not shaken) a liquid comprised in the reactor space can be/is distributed at least across the whole area of the bottom (3) of the vessel (1), thus, the liquid can be present throughout the whole cross section of the reactor space (according to the filling height).

In an embodiment (i) wherein the internal structure (4) comprises a wall having at least one opening (5), it is particularly preferred that said at least one opening (5) (e.g. one, two, three or four, or more of the openings (5)) are positioned in the area of the wall closest to the bottom (3). The "area closest to the bottom" is represented by the half of the wall in direction to the bottom (3), preferably the third of the wall, more preferred the fourth of the wall or the fifth of the wall in direction to the bottom (3). At least one opening (5) (or, if present, two, three or four or more openings (5)) can be placed at the lower end (the end coming in contact with the bottom (3)) of the internal structure so that the contact between the internal structure (4) and the bottom (3) is discontinuous so that the liquid present in the vessel (1) can enter the inner space of the internal structure (4). If opening(s) (5) are positioned at the lower end of internal structure (4) it is preferred that the opening(s) (5) have such a dimension that they allow the entrance/exit of the liquid to/from the inner space of the internal structure (4), however, leave at least 80% of the contact area between the lower end of internal structure (4) and bottom (3), preferably at least 85%, more preferred at least 90%, at least 95% and up to 97% or even up to 98% of the theoretical possible contact area between the internal structure lower end and the bottom (3). Thus, by the opening(s) said contact area is slightly interrupted. Examples of non-limiting embodiments of such structures are shown in FIGS. 1 to 8.

Said opening(s) (5) can have any shape selected from circular, half-circular, representing a circle sector, elliptic, half-elliptic, representing an oval sector, triangular, rectangular, polygonal, undulated or any combination thereof.

The opening(s) (5) preferably has/have a dimension (cross section in at least one direction) of at least 0.05 mm or at least 0.1 mm in any direction, e.g. at least 0.2 mm, at least 0.3 mm, at least 0.5 mm, at least 0.7 mm, 0.8 mm, 0.9 mm or at least 1 mm. It should be understood that the dimension of the opening(s) clearly depends from the total dimensions of the bioreactor vessel (1). The bigger the vessel, the bigger are the dimensions of the internal structure (4) and of the opening(s) (5). Thus, for a microreactor as commonly used in a µl-scale the opening(s) (5) might be very small, e.g. 0.1 mm or even smaller and up to a maximum of e.g. 0.5 mm or 0.8 mm. For big reactors provided for more than 1000 l culture liquid the opening(s) (5) can have a dimension of up to several cm, e.g. in the range of from 0.1 cm to 10 cm, from 0.4 cm to 8 cm, from 0.8 cm to 5 cm or any other suitable dimension. It should be understood that, if more than one opening is present, not all of the openings (5) have to have the same size/shape/dimension, but the openings can differ from each other (but don't have to).

Accordingly, dependent from the total dimensions of the bioreactor vessel (1) the opening(s) (5) of the internal structure (4) independently may have a shape and dimension providing cross sections in a range of from 0.1 mm to 10 cm or even lower or higher, if desired. The dimensions of the opening(s) (5) are only limited by the requirement to allow the liquid and the cells contained in the vessel (1) to enter/exit the inner space of the internal structure (4), but to maintain as much as possible of the surface area of surfaces (4a) and (4b).

If more than one opening is present, it is preferred that said openings (5) are non-uniformly distributed along the circumferential extend of the internal structure (4). If more than one opening is present, it is preferred that two "adjacent" openings are provided along the circumferential extend in an angle of from 20 to 120°, from 25 to 900 or from 30 to 60°, wherein said angle don't have to be the same between the openings, if more than two openings are present.

In an embodiment (ii) wherein the internal structure (4) is spaced apart from the bottom (3), the internal structure (4) has not necessarily opening(s) (5), but according to embodiment (iii) it can. If the internal structure (4) is spaced apart from bottom (3), the structure (4) can be hold in place by e.g. holding structures (7), which are attached on one end to the internal structure (4) and can be attached on the other end to the bottom (3) and/or to the outer vessel wall (2) or to any other suitable structure, e.g. to any closure (6). If the internal structure (4) is spaced apart from bottom (3) it should be understood that with "spaced apart" is meant that there is some free space between the lower end of the internal structure and the bottom (3), e.g. a narrow slot. Said slot should be so narrow that the liquid and the growing cells can pass, however, said liquid only in a very low extent compared to the whole liquid present in the bioreactor vessel (1). Accordingly, said slot can be as small as 0.05 mm, and up to 2 mm e.g. in vessels (1) with a capacity of more than 1000 l. It should be understood that the dimension of the space between the lower end of the internal structure (4) and the bottom (3) clearly depends from the total dimensions of the bioreactor vessel (1). The bigger the vessel, the bigger are the dimensions of the internal structure (4) and of the space between the lower end of the internal structure (4) and the bottom (3). Thus, for a microreactor as commonly used in a µl-scale the space might be very small, e.g. 0.05 mm or even smaller and up to a maximum of e.g. 0.3 mm. For big reactors provided for more than 1000 l culture liquid the space between the lower end of the internal structure (4) and the bottom (3) can have a dimension of up to some mm, e.g. in the range of from 0.5 to 2 mm or any other suitable dimension. Accordingly, dependent from the total dimensions of the bioreactor vessel (1) the space between the lower end of the internal structure (4) and the bottom (3) may have a dimension in a range of from 0.05 mm to 2 mm or even lower or higher, if desired.

The edges/borders of the opening(s) (5) or of the lower end of the internal structure (4) preferably are rounded so that there are no sharp ridges or rims where the cells growing in the reactor chamber can be damaged or injured.

According to the invention the internal structure provides at least two additional surfaces (4a, 4b) to the inner reactor space. These two additional surfaces may be represented by the outer surface (4a) and the inner surface (4b) of a wall of the internal structure (4). The internal structure (4) may also provide further walls and surfaces, but in a simple embodiment and for an easy understanding the invention is here explained with reference to one wall providing two surfaces (4a) and (4b). Further internal structures (4) providing additional surfaces may increase the here described effect(s).

The provision of at least two additional surfaces inside of the reactor chamber allows the increase of gas input into a liquid comprised in the bioreactor vessel, because said liquid comes not only in contact with the inner surface (2b) of the outer vessel wall (2), but further comes in contact with said additional surfaces (4a, 4b), in particular with said additional surface 4b. If a liquid comes in contact with a surface, the liquid spreads along said surface due to adhesion effects. If further the bioreactor vessel is shaken, preferably orbitally, the liquid bounces against the surface and is further floating along said surface, whereby the liquid surface coming into contact with gas present in the bioreactor vessel is increased. This effect is so much the better as the ratio between provided surface area of surfaces (2*b*), (4*a*) and (4*b*) and liquid volume increases. It can be understood that more gas can enter the liquid if the contact area between liquid and gas is increased. Thus, if the total surface area of surfaces inside the vessel (1)—which are surfaces (2*b*), (4*a*) and (4*b*)—coming in contact with the liquid is increased in the ratio to the total liquid volume, the bouncing and adhesion/floating effects enlarge the total area of contact between liquid and gas. Thereby the additional surface (4*b*) plays a major role compared to additional surface (4*a*), since the inner surfaces (2*b*) and (4*b*) are the surfaces, where along the liquid flows during operation, i.e. shaking of the vessel (1) in form of a "liquid sickle", corresponding to the bulk liquid. By providing said additional surface (4*b*) the number of liquid sickles increases, resulting in an increase of the contact area between the surfaces (2*b*, 4*b*) of the vessel (1) and the liquid, allowing the liquid to form a film along each of said surfaces during operating mode (shaking) of the vessel.

In a preferred embodiment the internal structure (4) provides surfaces (4*a*, 4*b*) at least a portion of which is parallel to the inner surface (2*b*) of the outer vessel wall (2). More preferred at least one of the surfaces (4*a*), (4*b*) is parallel to the inner surface (2*b*), preferably both.

The bioreactor vessel (1) can have the shape of any commonly known bioreactor vessel, e.g. the outer vessel wall (2) can have a cylindrical, conical, elliptic, oval, triangular, rectangular, polygonal or any other geometrical, regular or irregular basis shape (considered as its cross section). The internal structure (4) either can have the same or a similar shape as the outer vessel wall (2), wherein the dimensions are decreased, or the shape of the internal structure (4) differs from the outer vessel wall (2), but is also one of the before-mentioned. It is preferred that at least the shape of the internal structure (4) is represented by a cylindrical, conical or elliptic cross section, more preferred both, the internal structure (4) and the outer vessel wall (2) have such a cylindrical, conical or elliptic cross section, highly preferred is when both have a cylindrical shape.

The internal structure (4) is spaced apart from the inner vessel wall (2*b*) to provide an "outer part of the reactor chamber", which is the space between the inner surface (2*b*) of the outer vessel wall (2) and the outer surface (4*a*) of the internal structure (4). Thus, this outer part of the reactor chamber provides two surfaces to come in contact with the (cell culture) liquid, which are surfaces (2*b*) and (4*a*). The outer surface (4*a*) of the internal structure (4) is preferably spaced apart from the inner surface (2*b*) of the vessel wall (2) by at least $\frac{1}{15}$, or by at least $\frac{1}{12}$, or at least $\frac{1}{10}$, of the cross section of the total reactor chamber, but preferably not more than $\frac{1}{3}$, more preferred not more than $\frac{1}{4}$. even more preferred not more than $\frac{1}{5}$ or not more $\frac{1}{8}$ of the cross-section of the total inner space. In case the bioreactor vessel (1) has more than one internal structure (4), they can be spaced apart from each other in any distance, preferably in a distance as defined before, wherein it might be preferred that the internal structure(s) have almost the same distance to each other as the "first" internal structure (the internal structure closest to wall (2)) to the inner surface (2*b*). However, the distances may also vary, increase or decrease from the outer wall (2) in direction to the centre of the vessel (1).

In a preferred embodiment the outer surface (4*a*) of said internal structure (4) is spaced apart from the inner surface (2*b*) of the outer vessel wall (2) in a distance so that the ratio of the cross section of the internal structure ($CS_{in}$) to the cross section of the outer vessel wall ($CS_{out}$) is in the range of from 0.95 to 0.4, preferably in the range of from 0.92 to 0.5, more preferred in the range between 0, 9 and 0.55 and most preferred in the range of from 0.85 to 0.6, wherein said cross sections are measured along the bottom (3) in the space between the inner surfaces (2*b*) and (4*b*), respectively. It is particularly preferred that the outer vessel wall (2) and the internal structure (4) both have an essentially cylindrical form. The similar ratios of cross-sections can be assumed for more than one internal structure (4) present in the vessel, wherein $CS_{in}$ in this case corresponds to the cross section of the internal structure present closer to the centre of the vessel, whereas $CS_{out}$ represents the cross section of the internal structure present closer to the outer wall (2) in the vessel.

In bioreactor vessels of the above defined dimensions/ratios of the outer vessel wall (2) and the internal structure(s) (4) the gas exchange conditions inside the vessel are especially advantageous.

In an embodiment said internal structure(s) might have an internal cross section $CS_{in}$ of from 5 to 1200 mm, wherein said size depends from the whole dimensions of the bioreactor vessel (1). It should be understood that the dimensions of the internal structure(s) (4) depend from the dimensions of the bioreactor vessel (1)

The bioreactor vessel of the present invention can be represented e.g. by a single reactor in form of a container, a flask, a bottle, a pipe, a tube, a cup, a cell culture plate, or a bag, or it can be part of a multiarray with a plurality of individual vessels, like e.g. a multiwell plate, cell culture arrays or a microtiter plate. The bioreactor vessel might be a very small reactor vessel to be loaded with a liquid in an amount in the range of from 20 µl to 5 ml, but can also be a small reactor vessel to be loaded with a liquid in an amount ranging from more than 5 ml to about 100 ml, a mid-sized reactor vessel to be loaded with a liquid in an amount ranging from more than 100 ml to about 2 l, a large-sized reactor vessel to be loaded with a liquid in an amount ranging from more than 2 l to e.g. 10 l, or to an extremely large-sized reactor vessel to be loaded with a liquid in an amount of more than 10 l. The common sizes/dimensions of such vessels are well known to the skilled persons.

The bioreactor vessel (1), in particular the vessel wall (2) and the bottom (3) as well as the internal structure (4) and optional holding structures (7) can be made of any material commonly known to be used for the preparation of bioreactors, like any polymeric material, glass or metal, without being restricted to the mentioned. The vessel wall (2), the bottom (3) and the internal structure (4) as well as optional holding structures (7) can be made of the same material or of different materials, however are preferably made of the same material. Preferably the bioreactor vessel as a whole or part(s) thereof is/are made of glass or of a plastic material, e.g. polystyrene, polyethylene, polypropylene, polyamide, polyether, polyvinyl chloride, polyether sulfone or polyurethane, without being restricted to the mentioned polymeric materials, or of metal. Glass is a preferred material for the bioreactor vessel (1). Glass has a hydrophilic surface, which is readily wettable, thus, if the liquid during operation (shaking) of the reactor vessel flows along the glass surface, it forms a film on said surface due to the hydrophilic properties of the glass, said film provides suitable high gas exchange conditions. Alternatively, the bioreactor vessel (1) can be made of any of the before-mentioned materials and can be coated on the inner surfaces (e.g. at least on the surfaces 2*b* and 4*b*) with a hydrophilic coating material.

It is particularly preferred that at least the surfaces (2*b*), (4*a*) and (4*b*) are prepared from a material which is so hydrophilic that during shaking of the vessel the liquid comprised in the vessel forms a thin film on said surfaces, allowing gas exchange to a high extent.

The bioreactor vessel can further comprise a cover (6). Dependent from the type of bioreactor the cover can be a lid, a cover plate, a covering film, a closure head, a fastener, a plug, a covering cap or any other suitable closure means usually used for closing the bioreactor, wherein it is preferred that the cover is gas permeable or allows gas to enter the reactor chamber. For example, microtiter plates, multiwell plates or petri dishes often are closed by a covering plate, a film or a membrane. Containers, flasks, tubes or bottles commonly are closed by a lid, a plug, a cap or a screw closure.

Particularly if the cover (6) is closing the reactor chamber tightly, it might be suitable to provide the bioreactor vessel (1) or the closure (6) with an inlet and/or an outlet, allowing the addition or withdrawal of any content of the vessel or the placement of any measuring device inside of the vessel. Thus, nutrients, gas or liquids can be added to the vessel via an inlet, content of interest, e.g. the grown cells can be withdrawn by the outlet, even in a continuous manner.

The bioreactor vessel of the present invention can be used in any method involving the growing of biological cells, particularly in a liquid comprising cell culture, wherein it is necessary to have a high gas input into the liquid being in contact with the cells. Highly preferred the bioreactor may be used in a shaken liquid cell culture. Hereby the gas might be air, oxygen, carbon dioxide, nitrogen, a mixture comprising at least one of them, or any other desired gas. The gas preferably is an oxygen containing gas, more preferred the gas is air.

Thus, part of the invention is also a process for growing biological cells under defined gas conditions, wherein a bioreactor vessel (1) as defined in the disclosure above is provided with cells for growing and at least partially filled with a liquid culture medium and is shaken so that at least the liquid is rotationally moved inside the vessel. It is preferred that the cells to be grown are aerobic cells, however, if anaerobically growing cells should be grown, the present bioreactor vessel can also be used, it only has to assured that a suitable gas is provided within the reactor chamber. The bioreactor vessel is suitable for suspension cell cultures as well as for cell layer cultures, but suspension cell cultures are particularly preferred.

For culturing of cells the vessel (1) is filled with a liquid, e.g. the culture medium, in an amount so that in a non-operating state (vessel is not shaken) at least 50% of the orifices (5), preferably at least 75% of the orifices, even more preferred at least 90% of the orifices and most preferred all of the orifices of the internal structure (4) are immerged in the liquid. It is even preferred that not only the opening(s) are immerged in the liquid, but also that the liquid has contact with the surfaces (4*a*) and (4*b*) to an extent that during the rotation the liquid flows along said surfaces, thereby increasing the total surface area of the liquid.

FIGURES

In FIG. 1 a bioreactor vessel (1) is shown in an inclined top view, comprising an outer vessel wall (2), with an outer surface (2*a*) and an inner surface (2*b*), a bottom (3) and an internal structure (4) having an outer surface (4*a*) and an inner surface (4*b*) and three openings (5) circumferentially distributed at the lower end of the internal structure (4). The bioreactor vessel is shown without any cover (6).

FIG. 2 shows a similar embodiment as provided in FIG. 1, wherein the openings have not a triangle shape as in FIG. 1, but a square shape and the internal structure includes only two openings. Further, in this Figure it is illustrated how to define the cross sections $CS_{out}$ and $CS_{in}$ of the vessel (1). The outer cross section $CS_{out}$ corresponds to the total cross section defined by the inner surface (2*b*) of the outer vessel wall (2), the inner cross section $CS_{in}$ corresponds to the cross section defined by the inner surface (4*b*) of the internal structure (4).

EXAMPLES

Example 1: Experimental Design

Figure 1:
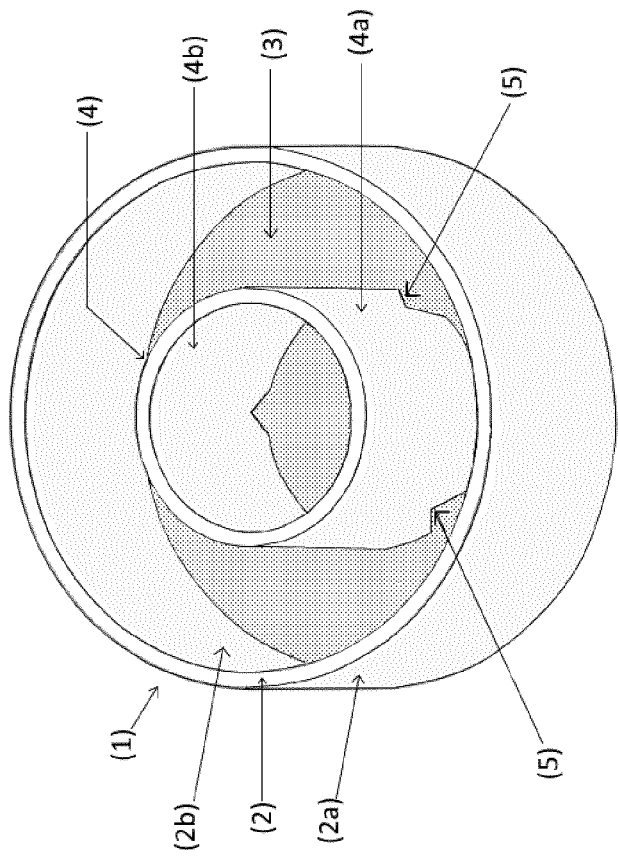
Figure 2:
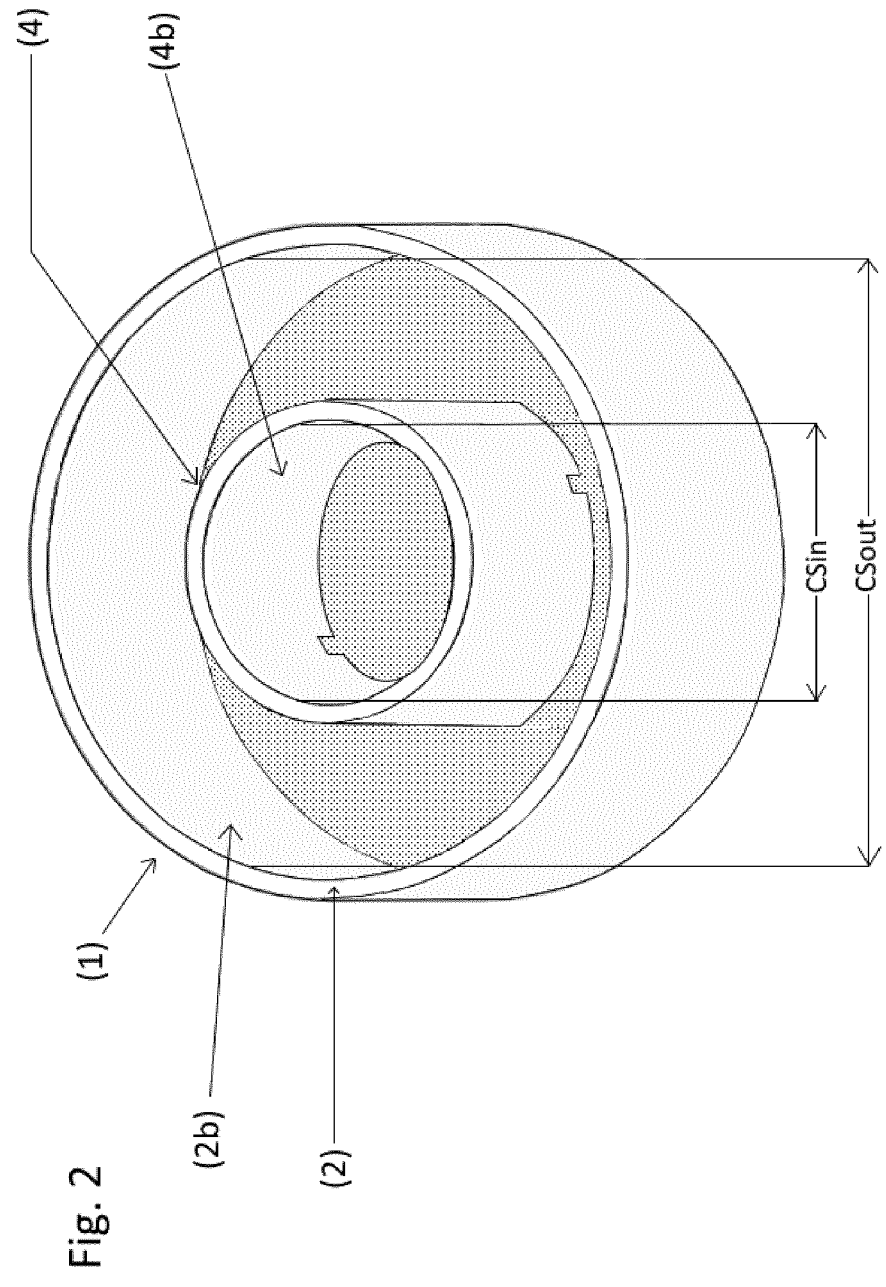
Figure 3:
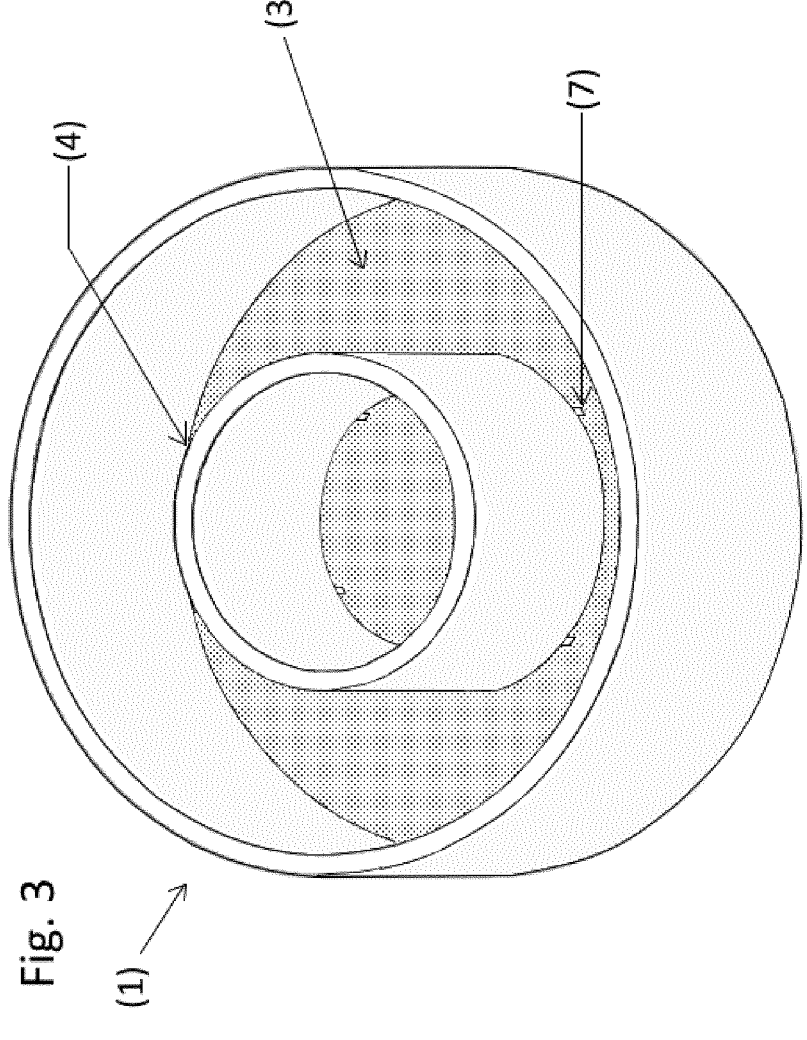
FIG. 3 shows a bioreactor vessel (1) in an inclined top view, wherein the internal structure (4) is spaced apart from the bottom (3) by holding structures (7).
Figure 4:
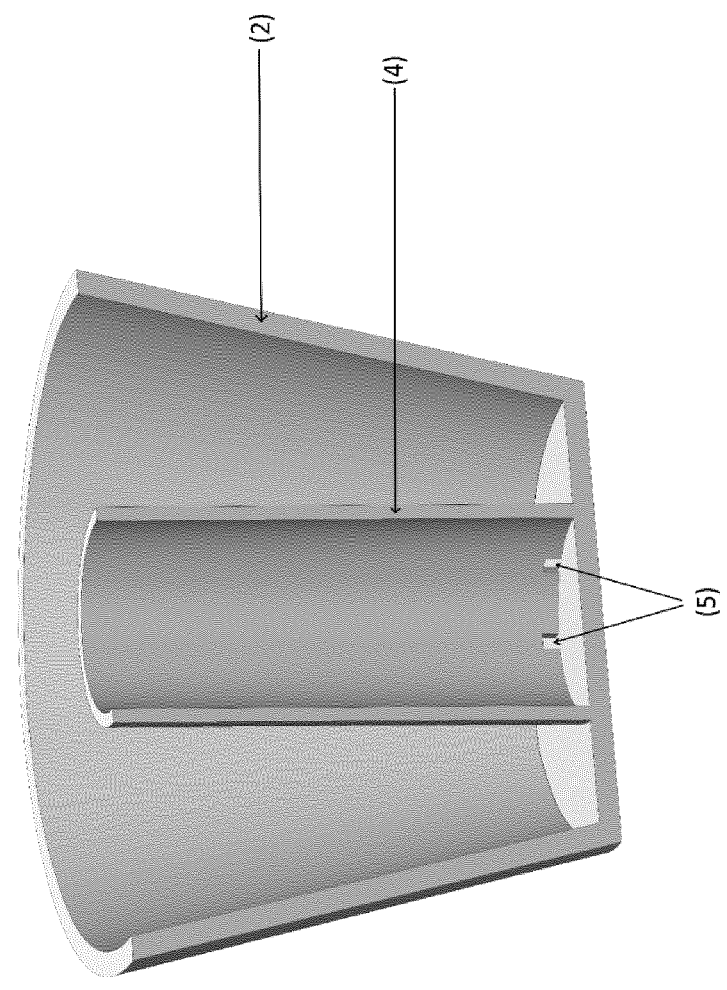
FIG. 4 shows a bioreactor vessel in a cross-sectional view, comprising an outer vessel wall (2), and an internal structure (4) having two openings (5) close to the bottom. The outer wall (2) and the internal structure (4) of the bioreactor vessel have a different geometrical shape (outer wall "top opening" conical, internal structure cylindric).
Figure 5:
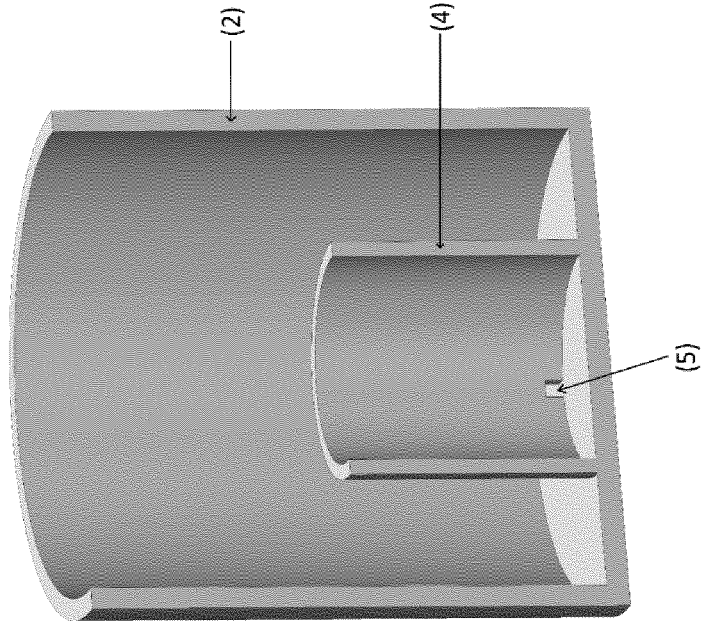
FIG. 5 shows a bioreactor vessel in a cross-sectional view, comprising an outer vessel wall (2), and an internal structure (4) having one opening (5) close to the bottom. The outer wall (2) and the internal structure (4) of the bioreactor vessel have the same geometrical shape, both cylindric, however, the internal structure (4) is shorter than the outer wall (2).
Figure 6:
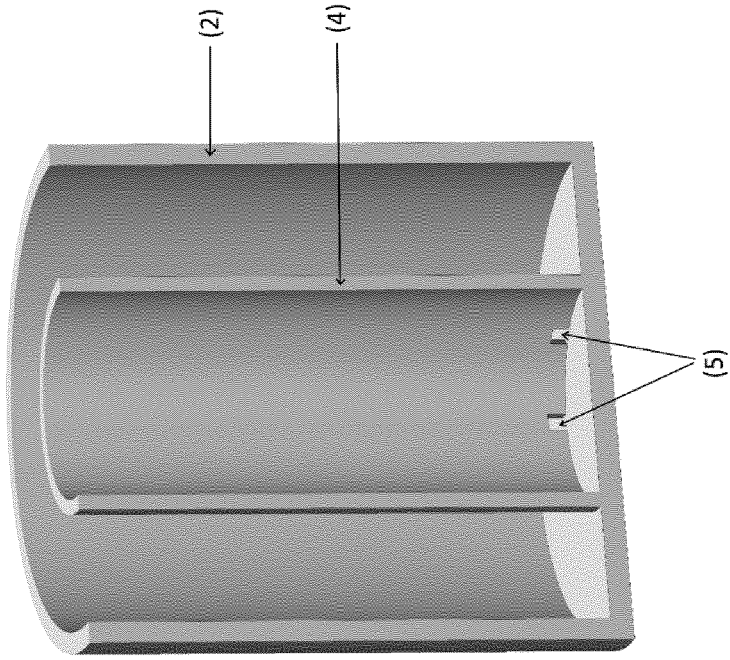
FIG. 6 shows a bioreactor vessel in a cross-sectional view, comprising an outer vessel wall (2), and an internal structure (4) having two openings (5) close to the bottom. The outer wall (2) and the internal structure (4) of the bioreactor vessel have the same geometrical shape, both cylindric, with the same height.
Figure 7:
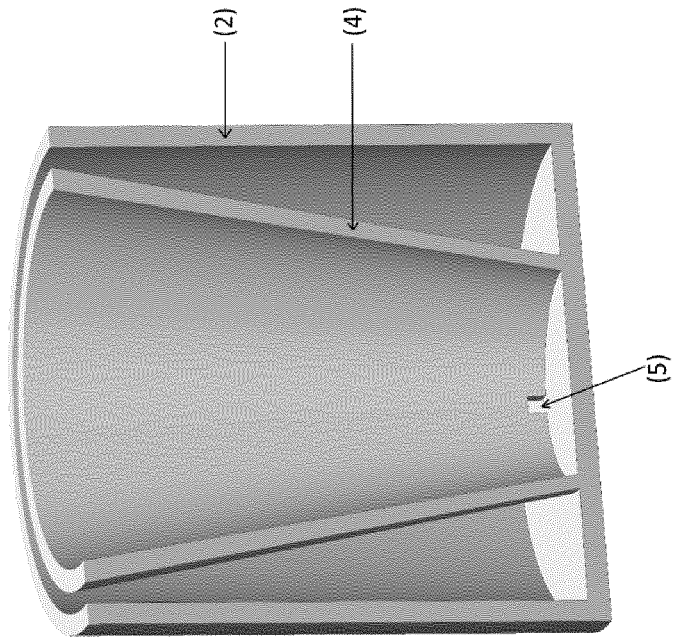
FIG. 7 shows a bioreactor vessel in a cross-sectional view, comprising an outer vessel wall (2), and an internal structure (4) having one opening (5) close to the bottom. The outer wall (2) and the internal structure (4) of the bioreactor vessel have a different geometrical shape (outer wall cylindric, internal structure "top opening" conical).
Figure 8:
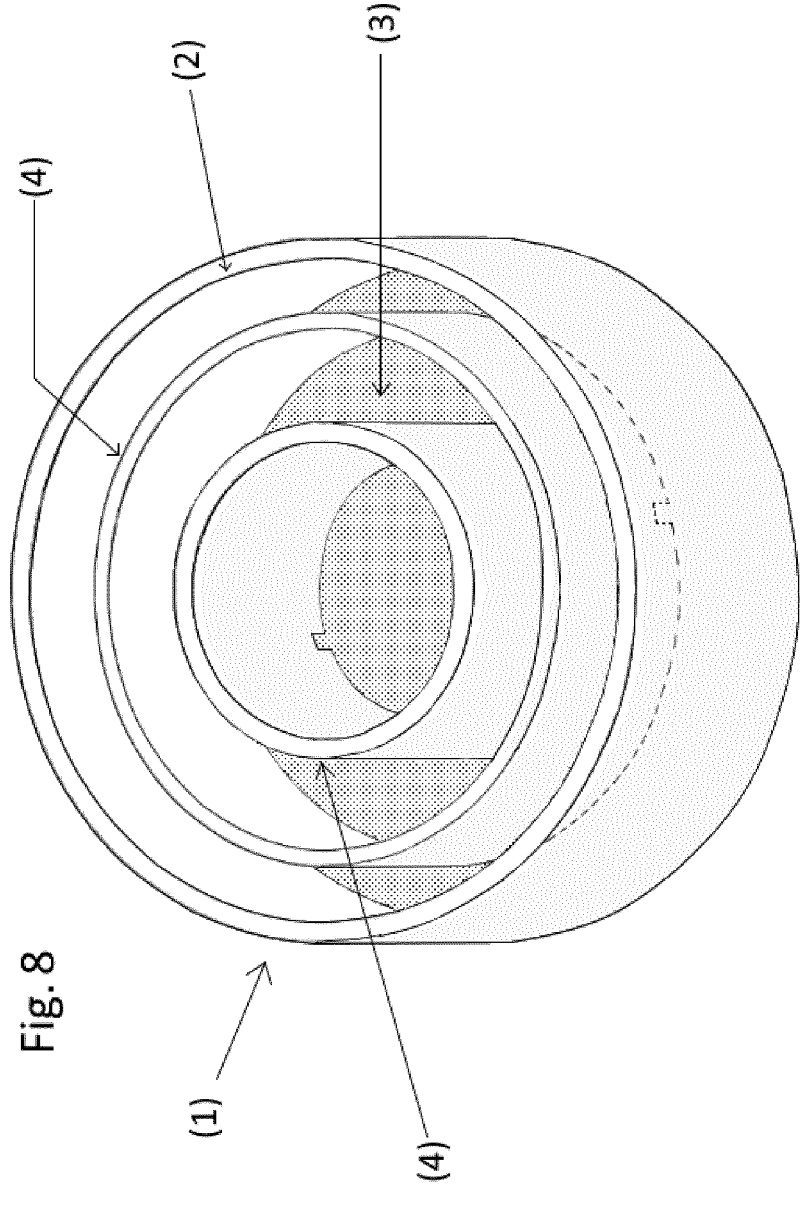
FIG. 8 shows a bioreactor vessel in an inclined side view, comprising an outer vessel wall (2), and two internal structures (4) having both one opening close to the bottom (3). The outer wall (2) and the internal structures (4) of the bioreactor vessel have all the same geometrical shape.

Three cylindric bioreactor vessel types have been prepared of glass having the following dimensions:

| Vessel Design | A Vessel without IS | B Vessel with IS (tight) | C Vessel with IS (wide) |
|---|---|---|---|
| Hight [mm] | 120 | 120 | 120 |
| Outer diameter of the vessel [mm] | 60.6 | 60.6 | 60.6 |
| Inner diameter of outer wall [mm] | 55.6 | 55.6 | 55.6 |
| Outer diameter of the IS [mm] | — | 44 | 38.1 |
| Inner diameter of the IS [mm] | — | 40.5 | 34.4 |
| Opening [mm in both directions]* | — | 2 | 2 |

IS = internal structure (cylindric)
*4 openings, each square-cut at the lower end of the internal structure The bioreactor vessels A, B, C have been filled respectively with the same liquid volume ($V_L$) as defined below and shaken under aerobic (air) conditions at 21° C. The oxygen transfer rate has been determined by the sulfite oxidation method as described in detail by Hermann R. et al. in the article "Optical method for the determination of the oxygen-transfer capacity of small bioreactors based on sulfite oxidation", published in Biotechnology and Bioengineering, Vol 74, No. 5, Sep. 5, 2001 (John Wiley & Sons, Inc)

Experimental Setting:

0.5 M sulfite oxidation method with detection of color change:

Shaker: Kuhner Lab Shaker LSR-V-12.5, shaking diameter $d_0=25$ mm

Sulfite system: 0.5 M $NaSO_3$ (Bernd Kraft, Duisburg, Germany) in 12 mM degassed phosphate buffer (from 0.5 M $Na_2HPO_4 \cdot 2H_2O$ and 0.5 M $NaH_2PO_4 \cdot 2H_2O$ (Roth, Karlsruhe, Germany), $2.4*10^{-5}$ M bromothymol blue (Sigma-Aldrich, Steinheim Germany), pH 8 with 30% $H_2SO_4$ (w/w) (Bernd Kraft, Duisburg, Germany), $10^{-7}$ M $CoSO_4 \cdot 7H_2O$ (Sigma-Aldrich, Steinheim Germany)

Sterile closure: Thomson Ultra Yield Flask AirOTop Enhanced Seal for Ultra Yield 2.5 L Flask (Thomson Instrument Company, Oceanside, USA)

Camera: Samsung Galaxy A3 (2016) with App "Interval-Cam"

$$Na_2SO_3^2 + \frac{1}{2}O_2 \xrightarrow{CO^{2+}} Na_2SO_4^2$$

$$OTR = c_{SO3} * \frac{v_{O2}}{t_{ox}}$$

$t_{ox}$=time till end of reaction (color change)
$v_{O2}$=stoichiometric coefficient of oxygen (0.5)
$c_{SO3}$=amount of sulfite used In the diagrams (FIGS. 9 to 11) showing the results of the present examples the internal structure is named "tube".

$OTR_{max}$: maximum oxygen transfer rate (capacity)

Example 2: Determination of $OTR_{max}$ Dependent from the Filling Volume $V_L$ In a first approach the oxygen transfer into the liquid is considered in dependency from the filling volume of the bioreactor vessels having the above described dimensions. Usually, the oxygen transfer capacity decreases when the volume increases, since the oxygen transfer occurs mainly at the liquid surface being in contact with the gas. The smaller the liquid volume, the greater is the ratio of liquid surface to liquid volume, if the liquid is provided in the same dimensioned vessel (as long as the whole bottom of the vessel is covered). Here, it is considered how the vessel design affects the oxygen transfer capacity.

The following samples have been tested (in vessel design A, B, C, respectively)

Figure 9:
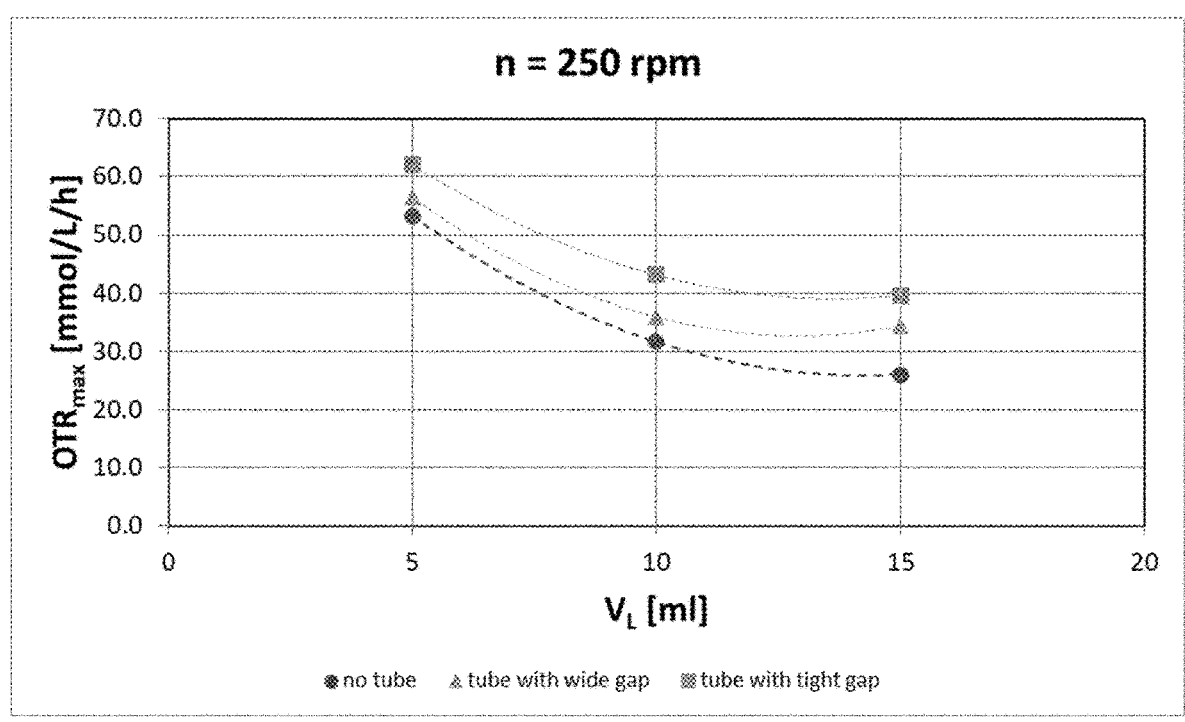
FIG. 9 shows a graph of the transfer rate (capacity) of oxygen into different volumes of a liquid, shaken in bioreactor vessels according to the invention in comparison to a common bioreactor vessel (see Examples 1 and 2)
Figure 9:
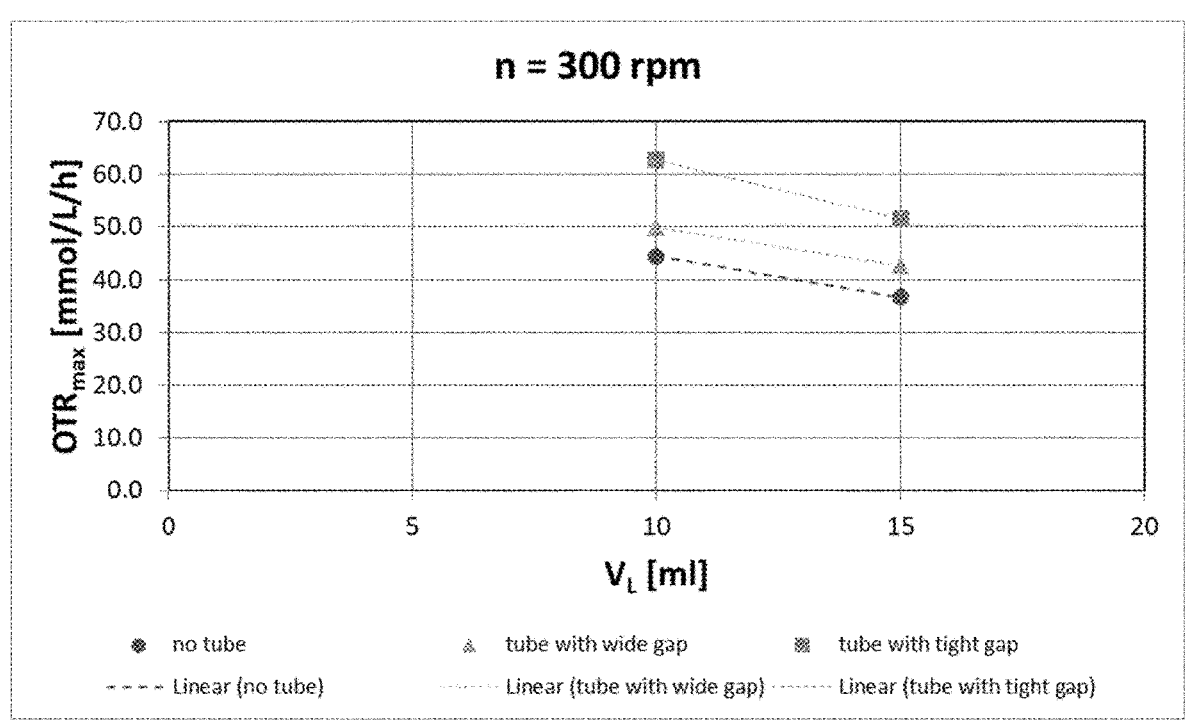

1. VL=5 ml, shaken at 250 rpm rotation
2. VL=10 ml, shaken at 250 rpm rotation
3. VL=15 ml, shaken at 250 rpm rotation
4. VL=10 ml, shaken at 300 rpm rotation
5. VL=15 ml, shaken at 300 rpm rotation FIG. 9 shows the results of the oxygen transfer capacity dependent from the filling volume of the vessels at two rotation speeds (FIG. 9A: 250 rpm, FIG. 9B: 300 rpm). As can be seen the oxygen transfer rate increases due to the presence of the internal structure ("tube"), wherein the tight gap between the outer wall of the vessel and the internal structure improves the $OTR_{max}$ noticeably stronger than the wider gap. Increasing the rotary speed increases the oxygen transfer rate noticeably (compare FIG. 9A to 9B)

Figure 10:
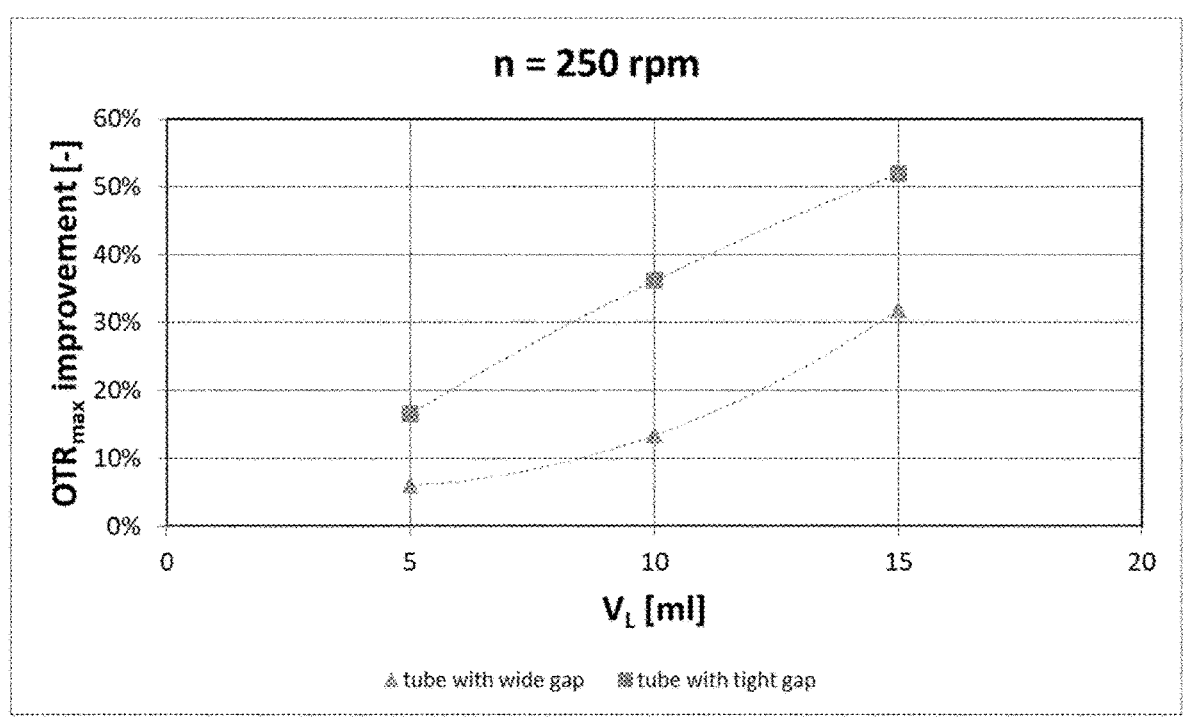
FIG. 10 shows a graph of the improvement of the oxygen transfer into a liquid, shaken in bioreactor vessels according to the invention (see Examples 1 and 2)
Figure 10:
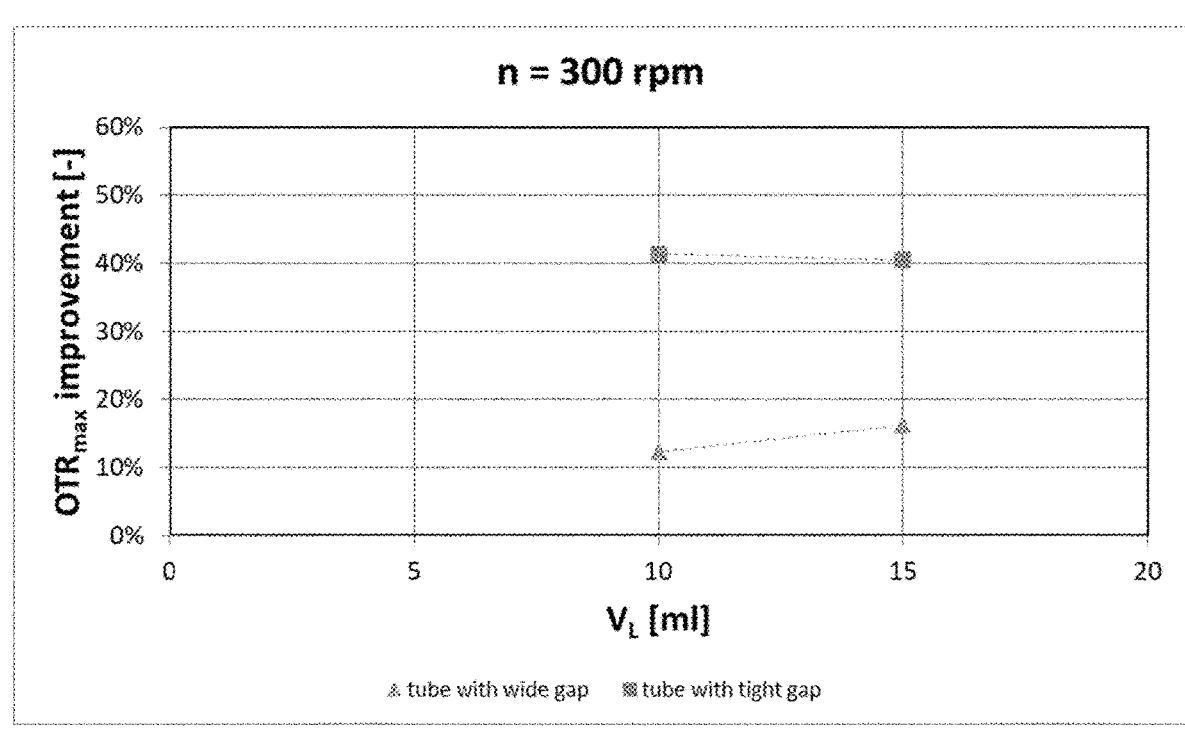

FIG. 10 shows the extent of improvement of the oxygen transfer obtainable by the inclusion of the internal structure (tube): In FIG. 10A it can be clearly seen that at 250 rpm the obtainable improvement of oxygen transfer is much stronger in a higher volume, in both the widely and the tightly gapped vessels. At 300 rpm the obtainable improvement is almost independent from the filling volume, see FIG. 10B. In both diagrams it is shown that the improvement obtainable with the smaller distance between outer wall and internal structure (tight gap) is noticeably higher than the improvement obtainable with the larger distance (wider gap). However, both designs have a clear positive effect to the oxygen transfer compared to the bioreactor without any internal structure.

Example 3: Determination of $OTR_{max}$ Dependent from the Rotational Speed n Further, the oxygen transfer into the liquid has been considered in dependency from the rotational speed (n) of the bioreactor vessels having the above described dimensions. It is basically known that the oxygen transfer capacity increases when the rotation speed increases, since the liquid is bouncing and flowing to a higher extent along the inner wall surface of the vessel, thus increasing the liquid surface area by forming a film on the inner surface of said wall. Since oxygen transfer occurs mainly at the liquid surface being in contact with the gas, the gas exchange increases when said surface is increased.

Figure 11:
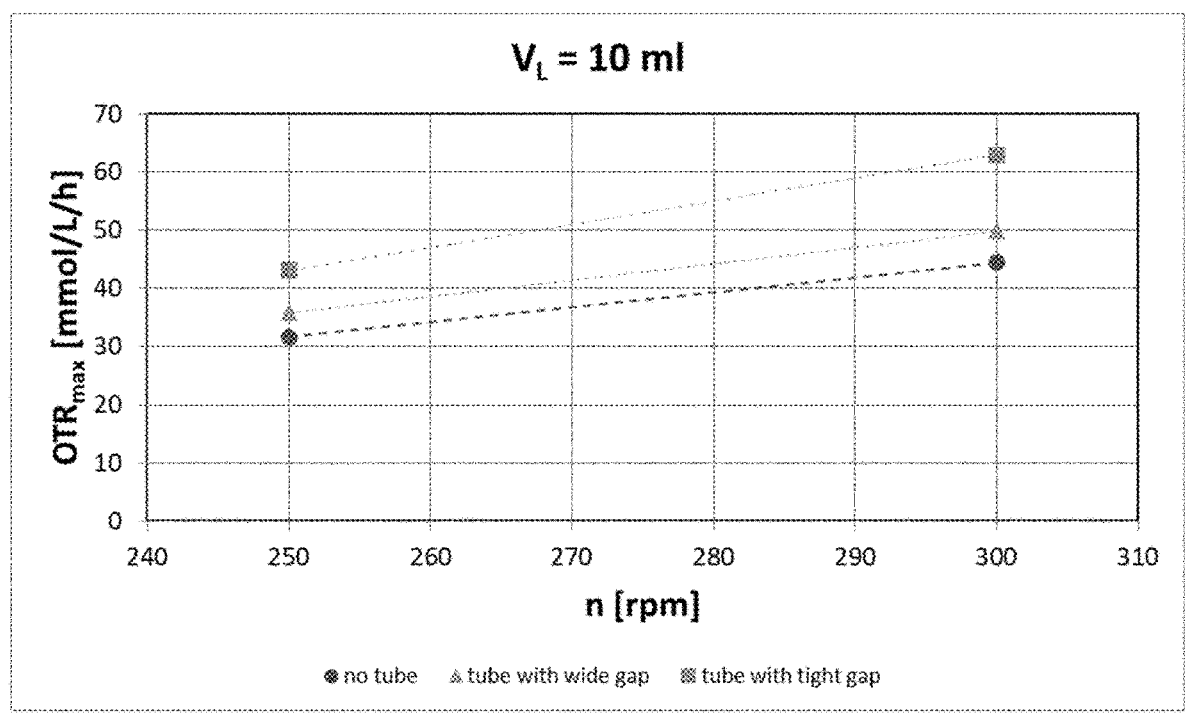
FIG. 11 shows a graph of the transfer rate (capacity) of oxygen into a liquid, shaken in bioreactor vessels according to the invention with different rotational speed. (see Examples 1 and 3).
Figure 11:
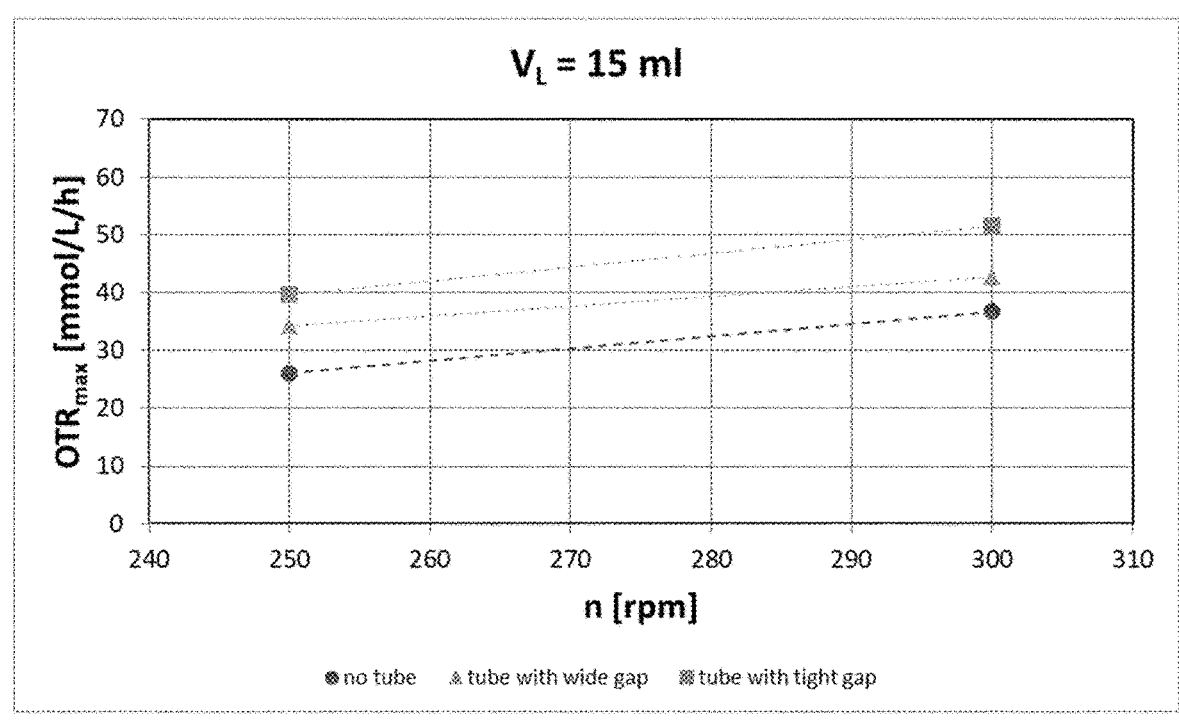

FIG. 11 A shows said improvement of oxygen transfer for samples 2 and 4, and FIG. 11 B for samples 3 and 5. As can be seen the provision of an internal structure providing additional surfaces increases the oxygen transfer into the liquid at both rotational speeds. The stronger effect of the tighter gap can be explained by the provision of a larger area of the additional inner surface (the inner surface of the internal structure) for forming a liquid film.

The dimensions and design of the bioreactor vessels shown in the above examples should be considered as illustrative. The particular sizes defined herein can be varied. Indeed, bioreactor vessels having larger or smaller dimensions can be prepared, however, it is particularly preferred that the proportions of the dimensions, especially the proportions of the walls, spaces, cross-sections and the size of the openings correspond essentially to the herein described dimensions.

The invention claimed is:

1. A process for growing biological cells under defined gas conditions, wherein said cells are grown in a bioreactor vessel (1) having an outer vessel wall (2) with an outer surface (2a) and an inner surface (2b), and a bottom (3), and further comprising at least one integrated internal structure (4) comprising a wall providing at least two additional surfaces, an outer surface (4a), and an inner surface (4b) to said vessel's inner reactor space, said internal structure (4), being spaced apart from said outer vessel wall (2), and wherein said wall of said internal structure (4):

(i) has at least one opening (5) in the area closest to the bottom (3) allowing cells to enter and exit the internal structure; or (ii) is spaced apart from the bottom (3); or (iii) has opening(s) allowing cells to enter and exit the internal structure and is spaced apart from the bottom (3);

and wherein said vessel is partially filled with liquid and is shaken so that the liquid moves rotationally between said outer vessel wall and said internal structure to form thin liquid films along the inner surface of the outer vessel wall and the outer surface (4a) and inner surface (4b) of the internal structure (4) to promote gas exchange.

2. The process of claim 1, wherein said opening(s) (5) and/or the space from the bottom (3) of the bioreactor vessel have/has a dimension of at least 0.05 mm in any direction.

3. The process of claim 1, wherein said opening(s) (5) have a shape selected from the group consisting of: circular, half-circular, elliptical, half-elliptical, triangular, rectangular, polygonal, undulated and any combination thereof.

4. The process of claim 1, wherein said at least one opening is located at the lower end of the internal structure (4) contacting the bottom (3) of the bioreactor vessel.

5. The process of claim 1, wherein said outer vessel wall (2) and said internal structure (4) have the same geometrical shape.

6. The process of claim 1, wherein said outer vessel wall (2) and said internal structure (4) have different geometrical shapes.

7. The process of claim 1, comprising more than one internal structure (4), so that more than two additional surfaces are provided within the vessel (1).

8. The process of claim 7, wherein the outer surface (4a) of the internal structure (4) is spaced apart from the inner surface (2b) of the vessel wall (2) by at least $\frac{1}{15}$, of the cross section of the inner reactor space.

9. The process of claim 7, wherein the outer surface (4a) of the internal structure (4) is spaced apart from the inner surface (2b) of the vessel wall (2) by at least $\frac{1}{10}$ of the cross section of the inner reactor space.

10. The process of claim 7, wherein the outer surface (4a) of said internal structure (4) is spaced apart from the inner surface (2b) of the outer vessel wall (2) at a distance such that the ratio of the cross section of the internal structure ($CS_{in}$) to the cross section of the outer vessel wall ($CS_{out}$) is in the range of from 0.95 to 0.4, and wherein said cross sections are measured along the bottom (3) in the space between inner surfaces (2b) and (4b), respectively.

11. The process of claim 1, wherein each internal structure:

a) is spaced apart from the inner surface (2b) of the vessel wall (2) by at least $\frac{1}{15}$ of the cross section of the inner reactor space; or b) is spaced apart from the inner surface (2b) of the outer vessel wall (2) at a distance such that the ratio of the cross section of internal structure ($CS_{in}$) to the cross section of the outer vessel wall ($CS_{out}$) is in the range of from 0.95 to 0.4, and wherein said cross sections are measured along the bottom (3) in the space between the inner surfaces (2b) and (4b), respectively.

12. The process of claim 1, wherein said bioreactor vessel is a single reactor in form of a container, a flask, a bottle, a pipe, a tube, a cup, or a bag, or is part of a multiarray with a plurality of individual vessels.

13. The process of claim 1, wherein the bioreactor vessel further comprises a cover (6).

14. The process of claim 1, further comprising an inlet and/or an outlet, allowing the addition or withdrawal of content of the vessel or the placement of a measuring device inside of the vessel.

15. The process of claim 1, wherein said biological cells, are bacteria, fungi, yeast, algae, archeae, animal cells, human cells, or plant cells.

16. The process of claim 2, wherein said at least one opening (5) is located at the lower end of the internal structure (4) contacting the bottom (3) of the bioreactor vessel.

17. The process of claim 16, wherein said outer vessel wall (2) and said internal structure (4) have the same geometrical shape.

18. The process of claim 16, wherein said outer vessel wall (2) and said internal structure (4) have different geometrical shapes.

19. The process of claim 2, comprising more than one internal structure (4), so that more than two additional surfaces are provided within the vessel (1).

20. The process of claim 19, wherein the outer surface (4a) of the internal structure (4) is spaced apart from the inner surface (2b) of the vessel wall (2) by at least $\frac{1}{15}$, of the cross section of the inner reactor space.

* * * * *